US 9,858,794 B2

(12) United States Patent
McCleary et al.

(10) Patent No.: US 9,858,794 B2
(45) Date of Patent: Jan. 2, 2018

(54) DETECTING AND NOTIFYING OF VARIOUS POTENTIAL HAZARDS

(71) Applicant: International Business Machines Corporation, Armonk, NY (US)

(72) Inventors: Donald W. McCleary, Denver, CO (US); Sal M. Rosato, Pine Plains, NY (US); Judith O. Uchidiuno, Catonsville, MD (US); Xiying Wang, Ithaca, NY (US); Justin D. Weisz, Stamford, CT (US)

(73) Assignee: International Business Machines Corporation, Armonk, NY (US)

( * ) Notice: Subject to any disclaimer, the term of this patent is extended or adjusted under 35 U.S.C. 154(b) by 135 days.

(21) Appl. No.: 14/672,354

(22) Filed: Mar. 30, 2015

(65) Prior Publication Data

US 2016/0292988 A1 Oct. 6, 2016

(51) Int. Cl.
*G08B 21/14* (2006.01)
*G08B 21/04* (2006.01)
(Continued)

(52) U.S. Cl.
CPC ............ *G08B 21/14* (2013.01); *A61B 5/1121* (2013.01); *A61B 5/6824* (2013.01);
(Continued)

(58) Field of Classification Search
CPC .................................................. H02J 7/0047
See application file for complete search history.

(56) References Cited

U.S. PATENT DOCUMENTS 6,031,454 A 2/2000 Lovejoy et al.
6,075,445 A 6/2000 McLoughlin et al.
(Continued)

FOREIGN PATENT DOCUMENTS

WO 2013027891 A1 2/2013

OTHER PUBLICATIONS

Schlangen, T., "Biological Hazard Alert System via Distributed Sensor Network," IP.com Prior Art Database Technical Disclosure, Aug. 30, 2007, © 2007 Motorola, Inc., IP.com No. 000157695.
(Continued)

*Primary Examiner* — Joseph Feild
*Assistant Examiner* — Pameshanand Mahase
(74) *Attorney, Agent, or Firm* — Joseph W. Cruz (57) ABSTRACT

A method for detecting and notifying of various potential hazards may include receiving a plurality of biometric data values by a first set of sensors of a sensing device. The biometric data values may correspond to a health state of a person. A plurality of environmental data values may be received by a second set of sensors of the sensing device. The environmental data values may correspond to a safety state of an environment that the person is in. The sensing device may compare the plurality of biometric data and environmental data values against respective models of biometric and environmental threshold data values that indicate a likelihood of a person or environment in an unhealthy or unsafe state. The sensing device may notify one or more communication devices if at least one of the biometric or environmental data values exceeds at least one of the threshold data values.

19 Claims, 6 Drawing Sheets

(51) Int. Cl.
 *A61B 5/11* (2006.01)
 *A61B 5/024* (2006.01)
 *A61B 5/053* (2006.01)
 *A61B 5/08* (2006.01)
 *A61B 5/00* (2006.01)

(52) U.S. Cl.
 CPC ..... G08B 21/0446 (2013.01); G08B 21/0453 (2013.01); *A61B 5/02438* (2013.01); *A61B 5/0531* (2013.01); *A61B 5/0816* (2013.01); *A61B 5/6802* (2013.01); *A61B 2560/0406* (2013.01)

(56) References Cited

U.S. PATENT DOCUMENTS

| | | | |
|---|---|---|---|
| 7,188,767 B2 * | 3/2007 | Penuela | G01D 1/18 235/435 |
| 8,013,734 B2 | 9/2011 | Saigh et al. | |
| 8,754,768 B2 | 6/2014 | Prieto | |
| 2005/0244013 A1 * | 11/2005 | Battenberg | G01H 11/00 381/57 |
| 2006/0252999 A1 | 11/2006 | Devaul et al. | |
| 2008/0088434 A1 | 4/2008 | Frieder et al. | |
| 2009/0054735 A1 * | 2/2009 | Higgins | A61B 5/0006 600/300 |
| 2011/0133927 A1 | 6/2011 | Humphrey et al. | |
| 2012/0172679 A1 | 7/2012 | Logan et al. | |
| 2013/0172722 A1 * | 7/2013 | Ninane | A61B 5/04085 600/383 |
| 2013/0237772 A1 | 9/2013 | Pisani et al. | |
| 2013/0278414 A1 * | 10/2013 | Sprigg | G08B 21/0453 340/539.12 |
| 2013/0317399 A1 * | 11/2013 | Ribble | G06F 19/3431 601/84 |
| 2014/0379588 A1 * | 12/2014 | Gates | G06Q 10/0631 705/308 |
| 2015/0332004 A1 * | 11/2015 | Najafi | G06F 19/345 706/46 |
| 2017/0049164 A1 * | 2/2017 | Gruentzig | A42B 3/046 |

OTHER PUBLICATIONS

Unknown, "About", LilyPad, http://lilypadarduino.org.
Unknown, "Gobetwino," MikMo, WordPress, http://mikmo.dk/gobetwino.html.

* cited by examiner

| Heatlh State Indicators | Biometric Data Values | Model Threshold Values Indicating an Unhealthy State | Biometric Data Values that Exceed Threshold Values |
|---|---|---|---|
| Heart Rate | 120 bpm | >100 bpm | ✓ |
| Oxygen Saturation | 82% | < 85% | ✓ |
| Respiration Rate | 34 rpm | < 12 rpm or > 20 rpm | ✓ |
| Skin Conductance | 0.62 µS | > 0.5 µS | ✓ |
| Acceleration Rate | 0g & 3.0g | < 0.3g or > 2.5g | ✓ |
| Angular Vel. | 800°/s | > 720°/s | ✓ |

| Environment State Indicators | Environment Data Values | Model Threshold Values Indicating an Unsafe Environment State | Environment Data Values that Exceed Threshold Values |
|---|---|---|---|
| Ambient Temperature | 50° F | <-30° F or >105° F | |
| Ambient Noise Level | 70 dB | > 90, 100, & 110 dB | |
| Ambient Light Level | 5 lux | < 1 lux | |
| Barometric Pressure | 29.92 in. | < 29.8 in. | |
| Hydrogen Sulfide Level | 110 ppm | > 100 ppm | ✓ |
| Ambient Oxygen Level | 20% | < 10% | |

DETECTING AND NOTIFYING OF VARIOUS POTENTIAL HAZARDS

BACKGROUND

This disclosure relates generally to wearable systems, and more specifically, to utilizing a wearable system to detect various hazards and notify one or more communication devices accordingly.

Workers may perform labor tasks in adverse environments, which may negatively impact the workers' health or work performance. For example, a boiler room mechanic may be exposed to high temperatures while repairing boilers. Consequently, the mechanic may suffer from dehydration, heat stroke, or exhaustion. In another example, a technician in a data center may be exposed to high noise levels, which may permanently impair hearing. In yet another example, a plant operator may be responsible for repairing very large units of equipment, which may require climbing several feet off the ground to repair the equipment. Consequently, the plant operator may fall from the equipment and suffer serious injury.

SUMMARY

A method, sensing device, and computer program product are provided. Some embodiments are directed to a sensing device for detecting and notifying of various hazards. The sensing device can include a plurality of biometric sensors configured to receive a plurality of biometric data values corresponding to a health state of a person. The plurality of biometric sensors may include at least a gyroscope sensor configured to measure an angular velocity of the person. The sensing device may also include a plurality of environmental sensors configured to receive a plurality of environmental data values corresponding to a safety state of an environment that the person is in. Further, the sensing device may include conductive threading configured to stitch-fasten at least the plurality of biometric sensors and the plurality of environmental sensors to an article of clothing, and further configured to provide communication channels for the plurality of biometric sensors and the plurality of environmental sensors. Moreover, the sensing device can include an analysis module configured to compare the plurality of biometric data values against a respective model of biometric data values, and further configured to compare the plurality of environmental data values against a respective model of environmental data values. The respective model of biometric data values may specify threshold data values that indicate a likelihood of a person in an unhealthy state. The respective model of environmental data values may specify threshold data values that indicate a likelihood that an environment is in an unsafe state. The sensing device may also include an alert module configured to notify one or more communication devices when the environmental data values or biometric data values exceeds the threshold data values that indicates a likelihood of a person in an unhealthy state or the threshold data values that indicates a likelihood that an environment is in an unsafe state.

In the Figures and the Detailed Description, like numbers refer to like elements. The drawings included in the present application are incorporated into, and form part of, the specification. They illustrate embodiments of the present invention and, along with the description, serve to explain the principles of the invention. The drawings are only illustrative of certain embodiments and do not limit the invention. While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

This disclosure relates generally to wearable systems, and more specifically, to utilizing a wearable system to detect various hazards and notify one or more communication devices accordingly. While the present disclosure is not necessarily limited to such application, various aspects of the disclosure may be appreciated through a discussion of various examples using this context.

When a person is working in a hazardous environment, he or she may underestimate the magnitude of danger presented by the environment. For example, a worker may be unaware that working at a particular noise level may cause permanent hearing loss when exposed for a particular amount of time. Accordingly, the worker may mistakenly wear single-use earplugs after being exposed to loud noise for eight hours, instead of wearing heavy-duty earmuffs needed after being exposed to loud noise for twenty minutes. Further, a worker may not be aware at all of the hazards that are presented in their working environment. For example, a worker may perform a work task in a confined space, which may be deficient of oxygen and include hydrogen sulfide toxic gases. However, the worker may initially be unaware of the oxygen deficiency or hydrogen sulfide gas. Although the Occupational Health and Safety Administration (OSHA) has introduced safety guidelines for workers operating in adverse environments, individual workers may be responsible for ensuring that they are following these guidelines.

Therefore, devices utilized for detecting potential hazards, and how a person is reacting to those hazards (e.g., biometric feedback) may be useful.

Although there are existing solutions for receiving biometric feedback or detecting environmental hazards, such solutions may not provide flexible sensing device circuitry resulting in a low profile and comfortable fit. This may be important for a worker performing arduous tasks throughout his or her work day. Further, no solutions may exist to provide a complete picture of a worker's biometric characteristics and the environment that the worker is in (i.e., solutions may not include enough biometric and environmental sensing data to get an adequate reading of health and environmental characteristics). Particularly, solutions may not fully provide adequate motion sensing data of a worker, who for example, may fall from a large unit of equipment and experience varied movements. Accordingly, embodiments of the present disclosure are directed to a flexible and wearable sensing device that may receive a plurality of biometric data values of a person via biometric sensors (e.g., angular velocity of a person, acceleration rate of a person, heart rate, respiration rate, etc.), and a plurality of environmental data values of the environment that the person is working in via environmental sensors (e.g., toxic gas level, ambient temperature, ambient noise level, etc.). The sensing device may compare the data values against model threshold data values (e.g., OSHA safety guidelines) that indicate when a person or environment is likely in an unhealthy or unsafe state. The device may then notify one or more communication devices (e.g., smart phones, smart watches, etc.) when the biometric or environmental values exceed model threshold values. The sensing device may also include conductive threading configured to stitch-fasten the plurality of biometric sensors and the plurality of environmental sensors to an article of clothing. The conductive threading may be further configured to provide communication channels for the plurality of biometric sensors and the plurality of environmental sensors. Therefore, the conductive threading may allow for increased flexibility of the sensing device and a relatively low profile such that a worker may experience increased comfort and range of motion.

The term "exceed" (or "outside of," "surpass," or the like) as disclosed herein, refers to any biometric or environmental data values that are below a low model threshold data value, or above a high model threshold data value. For example, a respiratory rate model of threshold values may indicate a likely unhealthy state when either the biometric data values are less than 12 respirations per minute (rpm) or more than 20 rpm. In this illustration, 5 rpm would "exceed" a low threshold (i.e., 5 rpm is below the 12 rpm threshold), and 30 rpm would "exceed" the high threshold (i.e., 30 rpm is above the 20 rpm threshold).

Figure 1:
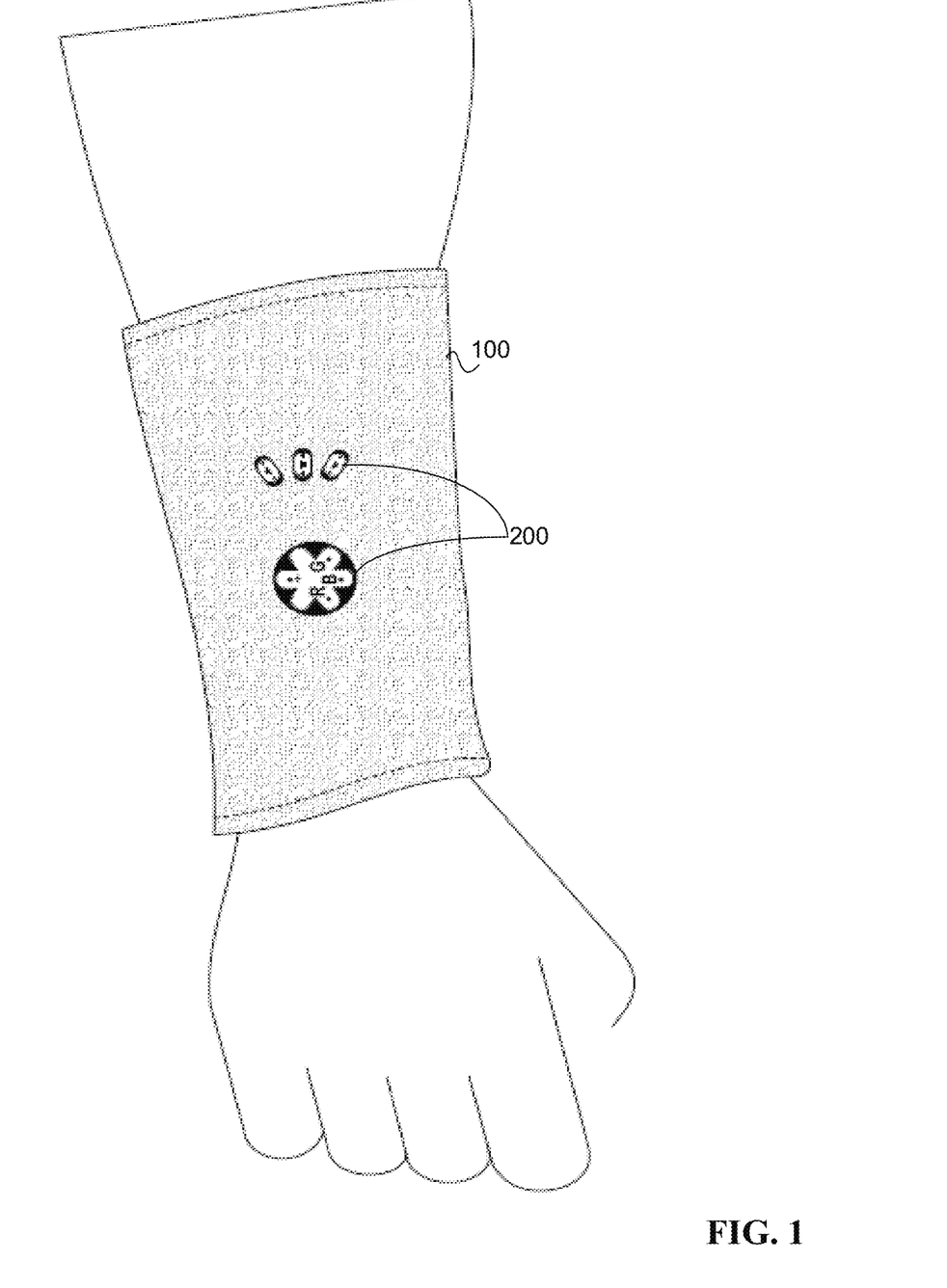
FIG. 1 illustrates a wearable sensing device stitch-fastened to an armband according to an embodiment of the present disclosure.

FIG. 1 illustrates a wearable sensing device stitch-fastened to an armband according to an embodiment of the present disclosure. The wearable sensing device 200 may receive a plurality of biometric data values by a first set of sensors of the sensing device, the biometric data values corresponding to a health state of a person. The sensing device 200 may also receive a plurality of environmental data values by a second set of sensors of the sensing device, the environmental data values corresponding to a safety state of an environment that the person is in. The sensing device 200 may also compare the plurality of biometric data values against a respective model of biometric data values and compare the plurality of environmental data values against a respective model of environmental data values, the respective model of biometric data values specifying threshold data values that indicate a likelihood of a person in an unhealthy state and the respective model of environmental data values specifying threshold data values that indicate a likelihood that an environment is in an unsafe state. In response to the comparing, the sensing device 200 may also determine whether at least one of the biometric or environmental data values exceeds the threshold data values. Further, the sensing device 200 may be configured to notify one or more communication devices that at least one of the biometric or environmental data values meets at least one of the threshold data values. Further details regarding these steps are discussed below.

Although the embodiment in FIG. 1 illustrates that the sensing device 200 is embedded in an armband 100, the sensing device 200 may be embedded in various other articles of clothing or wearable apparel. For example, the apparel may be a glove to provide a more accurate reading by the sensing device 200 (e.g., a pulse oximeter sensor located in an anterior-distal finger section of the glove may provide an optimal reading of blood oxygen levels when attached to the finger). The apparel may also be ear muffs, leg bands, head bands, shirts, pants, shoes, socks, or any other suitable apparel for embedding the sensing device 200 and retrieving readings of biometric and environmental data.

Figure 2:
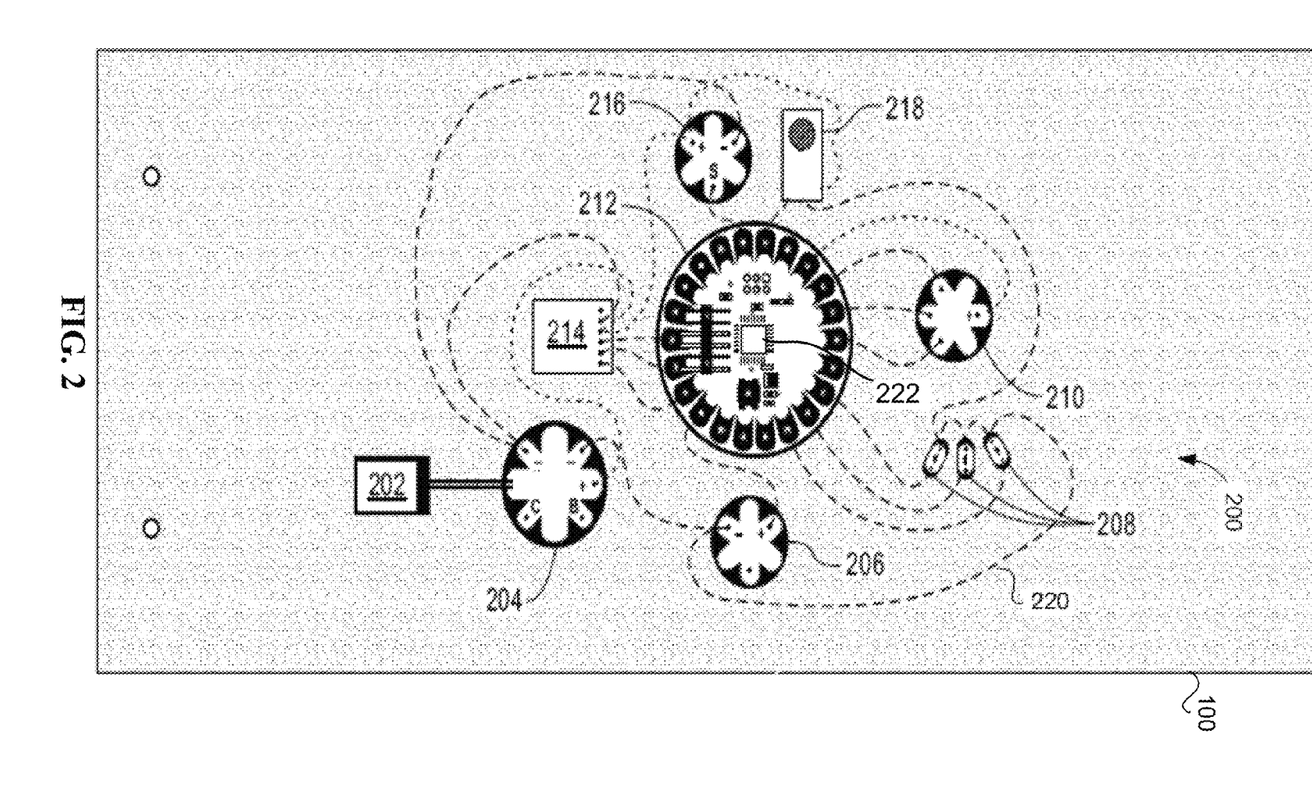
FIG. 2 is an illustration of an example sensing device circuit according to an embodiment of the present disclosure.

FIG. 2 is an illustration of an example sensing device 200 according to an embodiment of the present disclosure. The sensing device 200 may be a circuit that is stitch-fastened to the armband 100. The sensing device 200 may include a microcontroller board 212 that houses a microcontroller 222, a plurality of environmental sensors, which may include a toxic gas level sensor 216, and a microphone 218. The sensing device 200 may also include a plurality of biometric sensors, which may include an accelerometer 210 and a gyroscope 206. The sensing device 200 may also include a set of light emitting diodes (LEDs) 208, a memory card 214 (e.g., a Secure Digital (SD) memory card), a battery 202, a battery holder 204, and conductive threading 220. In some embodiments, the sensing device 200 may also include a radio (not shown). The sensing device 200 may be any suitable configuration to allow for flexibility and sensing of biometric and environmental data (e.g., LilyPad Arduino, E-textile based circuits, etc.)

The microcontroller 222 may be a small computing device utilized to sense biometric and environmental inputs, and communicate the input results to one or more output devices (e.g., LEDs 208 to flash in case any biometric or environmental data values exceeds model threshold values). In an embodiment, the microcontroller 222 may include a memory (which may be the memory card 214) to store and access data, a processor to execute data programs, an oscillator (and corresponding counters and timers) to monitor the quantity and rate of pulse signals for frequency stabilization, and a plurality of input/output (I/O) pins to connect with peripherals (e.g., biometric and environmental sensors, radios, LED's, switches, relays, solenoids, etc.). The microcontroller 222 may positioned on a microcontroller board 212. In embodiments, the microcontroller board is flexible material (e.g., felt, fabric, or card stock) to allow greater flexibility for the sensing device 200.

The sensing device 200 may also include a plurality of sensors for sensing particular biometric and environmental data. Each of the plurality of sensors may be connected to a respective I/O pin of the microcontroller 222. Each sensor that is connected to the pin may include respective input modules (e.g., electrode skin conductance reader or temperature reader for receiving biometric or environmental data). The sensors may be any suitable sensor for receiving biometric or environmental data values to determine a health state of a person or a safety state of an environment the person is in. For example, the biometric sensors may be an accelerometer 210, which is used for measuring acceleration of a person, a gyroscope 206, used for measuring the angular velocity of a person, a pulse oximeter, which is used for measuring oxygen saturation levels, heart rate, and respiration rate, or skin conductance sensors, which are used for measuring physiological or psychological arousal. The environmental sensors may include a temperature sensor 216, a microphone 218, which is used for detecting noise level, electromagnetic sensor, barometric sensor, which is used to detect air pressure for weather forecasting, toxic gas sensor, flammability sensor (not shown), or any other suitable sensor for embodiments of the present disclosure. These various sensors will be described in more detail below.

In an embodiment, the memory card 214 may be utilized for logging the plurality of biometric and environmental data values received by the sensing device. The memory card 214 may also be utilized to log models of biometric and environmental data (e.g., Occupational and Safety and Health Administration (OSHA) acceptable noise level standards). In various embodiments, the memory card 214 may be any suitable type of memory and may include a memory attached to the microcontroller board 212. The memory may be a random-access semiconductor memory, storage device, or storage medium (either volatile or non-volatile) for storing or encoding data and programs. In another embodiment, the memory represents the entire virtual memory of the sensing device, and may also include the virtual memory of other systems coupled to the sensing device or connected via a network. The memory card 214 may be a single monolithic entity, but in other embodiments the memory card 214 may include a hierarchy of caches and other memory devices. For example, memory may exist in multiple levels of caches, and these caches may be further divided by function, so that one cache holds instructions while another holds non-instruction data, which is used by the processor (e.g., Read only Memory (ROM) to permanently store memory or Special Function Registers (SFR) as part of Random Access Memory (RAM) to control the function of pins used for temporarily storing data). The memory card 214 may be further distributed and associated with different CPUs or sets of CPUs.

Figure 4:
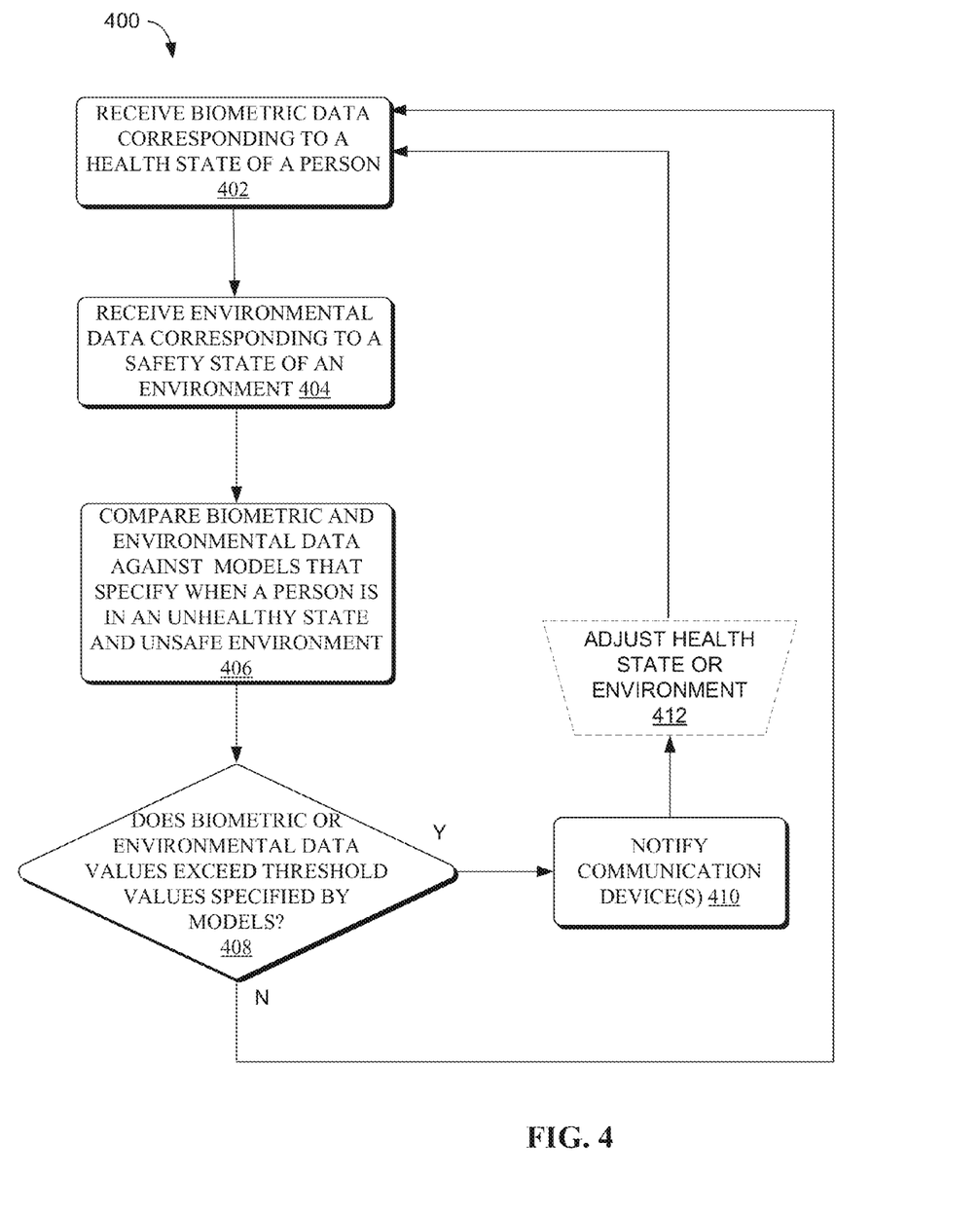
FIG. 4 is a flow diagram of an example process for detecting various biometric and environmental hazards and notifying one or more communication devices accordingly, with respect to various embodiments.

The memory card 214 may store all or a portion of the data or programs responsible for executing process 400 of FIG. 4. In one embodiment, the programs and data structures may be included within the memory card 214 in the sensing device. However, in other embodiments, some or all of them may be on different computing systems and may be accessed remotely, e.g., via a network. The sensing device may use virtual addressing mechanisms that allow the programs of the sensing device to behave as if they only have access to a large, single storage entity instead of access to multiple, smaller storage entities.

In an embodiment, the memory card 214 may include instructions or statements that execute on the processor within the microcontroller or instructions or statements that are interpreted by instructions or statements that execute a processor to carry out the functions as further described below. In another embodiment, the components may be implemented in hardware via semiconductor devices, chips, logical gates, circuits, circuit cards, and/or other physical hardware devices in lieu of, or in addition to, a processor-based system. In various embodiments, the memory card 214 may include an analysis module, which may be configured to compare the plurality of biometric data values and the plurality of environmental data values against models of biometric data values and models of environmental data values. The models of biometric and environmental data values may specify threshold data values that indicate a likelihood that a person is in an unhealthy state and indicate a likelihood that an environment is in an unsafe state. The analysis engine may determine which of the plurality of biometric data values or the plurality of environmental data values exceeds the threshold data values. This may be done to later notify one or more communication devices when a set of values of the plurality of biometric data values or set of the plurality of environment al data values exceeds the threshold data values.

The memory card 214 may also include an alert module to determine which devices to notify when threshold data values have been exceeded. For example, if a person was only breathing in 8% oxygen, and a model threshold value indicates unsafe oxygen levels are anything less than 10%, the sensing device may send a notification, but the alert module may have preprogrammed device destinations of what devices it will transmit notifications to. For example, the mobile phones of an entire working crew, including a supervisor mobile phone may be notified.

LEDs 208 may be utilized as an output device to communicate the input results to in case any biometric or environmental data values exceeds model threshold values (e.g., flashing to notify the wearer that corresponding inputs indicate potential danger based on model values). In one or more embodiments, the LEDs 208 may be tri-color LEDS. In these embodiments, there may be different colors of LEDs that correspond to particular states. For example, a green LED may flash to indicate that the outside temperature is below 80 degrees Fahrenheit. A yellow LED may flash to indicate that the temperature is above 80 degrees but below 100 degrees Fahrenheit. A red LED may flash to indicate that the environment is 100 degrees Fahrenheit or greater, which may exceeds a model threshold value such that the sensing device may notify one or more communication devices of the potential heat danger. These indicators may notify a worker to be more cautious about working in elevated temperatures and to take appropriate breaks when needed.

In one or more embodiments, the LEDs 208 may be a single set of white LEDS that may correspond to different states. For example, a first LED may flash if the ambient noise level is less than 80 decibels (dBs). A first and second LED may flash if the noise level exceeds 80 dBs, but is below 115 dBs. A first, second, and third LED (i.e., the entire set of LEDs) may flash if the noise level exceed 115 dBs. 115 dBs is the threshold limit, according to OSHA, at which point a person must put on proper hearing equipment within fifteen minutes to mitigate the risk of permanent hearing loss. Accordingly, 115 dBs may be the threshold value at which, all three white LEDS may flash to warn a worker that he or she must immediately put on ear protection.

A vibration motor (not shown) may alternatively be implemented as an output device to which an input sensor communicates to in case any biometric or environmental data values exceeds model threshold values. In an embodiment, a vibration motor (e.g., a vibe board) may be Direct Current (DC) coreless motor that when given a signal by a sensing device, will vibrate due to an asymmetric mass attached to a drive shaft. This may notify the person wearing the sensing device that the environment or person is at a particular state or health. For example, if the noise level reaches 115 dBs or more, the vibration motor may vibrate. This may be utilized to notify the worker that he or she must immediately place ear muffs on. The vibration motor may be a cylinder configuration, coin configuration, or any other suitable configuration.

In an embodiment, a radio (not shown) (e.g., xBee radio) may be utilized by the sensing device to establish a connection with one or more remote devices and notify the one or more communication devices when the plurality of biometric data values or the plurality of environmental data values exceeds the threshold data values. The radio may include a transmitter for transmitting the notifications and a receiver for receiving feedback (e.g., via a central server that notifies the sensing device when particular biometric or environmental states have been reached). In an illustrative example, when a person exceeds an acceleration threshold and an angular velocity threshold, suggesting that a person has fallen and tumbled from a building, the sensing device may transmit a notification through a radio transmitter to a mobile device of a supervisor, with indicia describing that a particular worker has likely fallen from a large building. This may accordingly allow for the immediate help of the worker in distress.

In various embodiments, the sensing device 200 may also include a switch (not shown) to turn off any feedback notification signals. For example, if a notification has been sent because the ambient temperature is above a model threshold value (e.g., 105° F.), and the worker has already taken appropriate precautions (e.g., taken a break, drank water, rested, etc.), then the worker may press the switch on the sensing device such that the alarm will no longer provide feedback. The switch may be configured to stop feedback notifications, notifications to secondary devices located on the person (e.g., smartphone, smart watch, etc.), or notifications to external devices located on other persons (e.g., smartphone of a supervisor).

In an embodiment, conductive threading 220 may be utilized to connect all of the different components above (e.g., batter holder 204, gyroscope 206, set of LEDs 208, accelerometer 210, memory card 214, toxic gas sensor 216, and microphone 218) to the desired apparel and the microcontroller board 212. Therefore, conductive threading 220 may be configured to stitch-fasten (e.g., sew) all of the components above to an article of clothing, and further configured to provide communication channels for the plurality of biometric sensors and the plurality of environmental sensors. Conductive threading 220 is a set of thin conductive wires (e.g., 2 ply stainless steel threads) that carry current to perform various operations as described in the present disclosure. In one or more embodiments, each of the components above may include apertures lined with conductive material designed to receive the conductive threading 220 to make the desired connections (i.e., the conductive threading may pass through the apertures to allow for suitable connections). Accordingly, a person may sew the sensing device 200 together, which may create flexible circuits that require little or no soldering. In embodiments, the types of conductive threading 220 may be any suitable type for using E-textile based circuits. For example, the conductive threading 220 may be stainless steel, silver, silver coated, or any other threading depending on the amount of resistance needed. In an illustrative example, a person may tie the conductive threading 200 to a needle and run the needle through a battery holder 204 aperture and the desired apparel immediately beneath the battery holder 204 so as to sew the battery holder to the apparel. The person may then make a connection from the battery holder 204 to a pedal of the microcontroller board 212 by sewing in a linear manner from the battery holder 204 to the microcontroller board 212 pedal aperture. The person may then run the needle through the pedal aperture and apparel immediately beneath the pedal aperture several times to sew the pedal aperture to the apparel. This process may be repeated for connecting other components to the microcontroller board 212. In various embodiments, manual sewing, sewing machines, or other methods of making connections between components may be performed. In other embodiments, different wire connections may be utilized instead of conductive threading, such as 0.5 millimeter (mm) electrical wires insulated with rubber or plastic coating.

Figure 3:
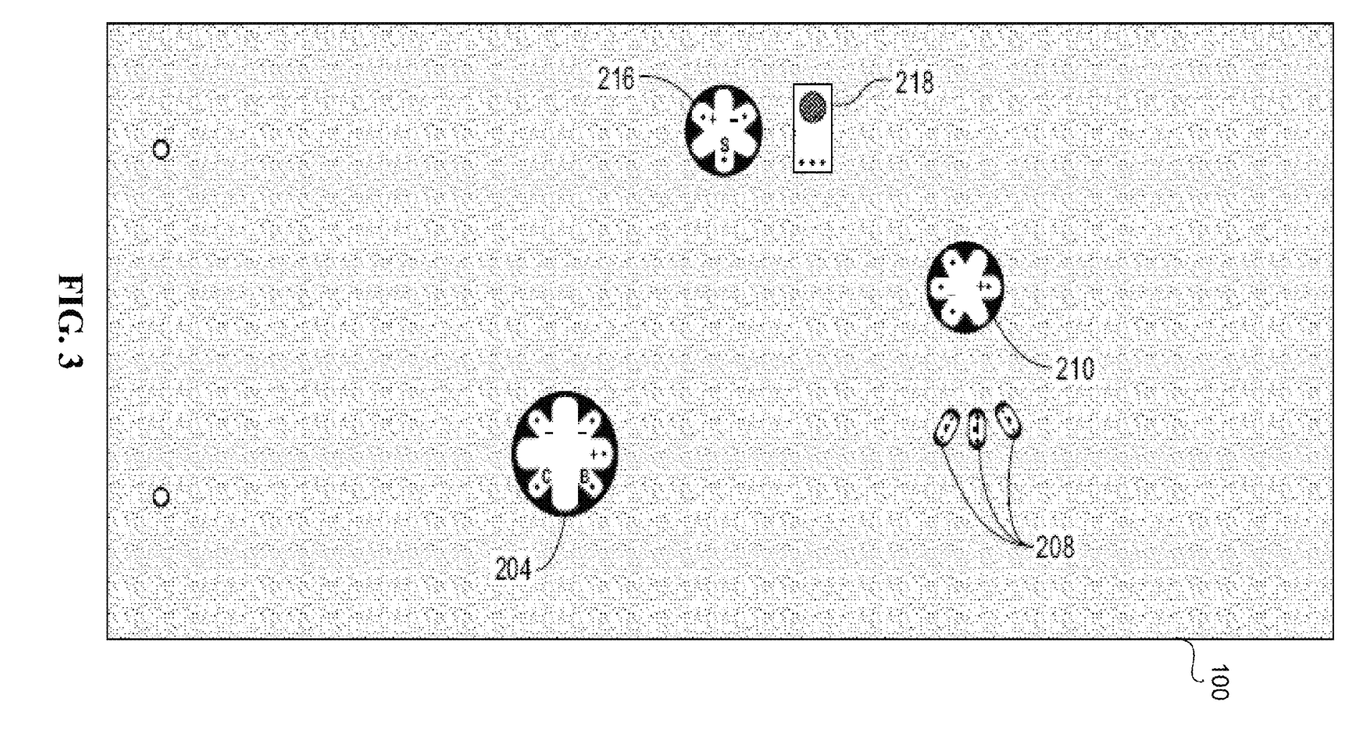
FIG. 3 is an illustrative example of the sensing device circuit of FIG. 2, which shows what components of the sensing device circuit may be visible to a user wearing the sensing device, according to an embodiment.

FIG. 3 is an illustrative example of the sensing device circuit of FIG. 2, which shows components of the sensing device circuit that may be visible to a user wearing the sensing device, according to an embodiment. The sensing device 200 may include various components that are visible by a user such that the user may interact with the components and/or the sensing device may take efficient readings of the user or environment that the user is in. For example, the temperature sensor 216 may visibly protrude from the armband 100 to effectively gauge the ambient temperature of the environment that the user is in. Likewise, the microphone 218 may visibly protrude from the armband 100 to effectively gauge the noise level of the environment that the user is in. A portion of the battery holder 204 may be visible to the user so that the user may use an on and off switch for the sensing device. A set of LEDs 208 may also be visible such that a user may receive visual feedback for the user's health state or environmental state that the user is in. An alert switch (not shown) may also be visible to a user such that the user may be able to turn off unnecessary notifications (e.g., turn off LEDs, audible alarm, etc.). Other component sensors may also be visible, such as an accelerometer 210. In these embodiments, the desired apparel may be sewn over the rest of the components in FIG. 2 (e.g., battery 202, gyroscope 206, microcontroller board 212 and microcontroller, and memory card 214). The user may desire that some components remain concealed to provide for a low profile of the sensing device 200 such that there is a decreased chance that sensing device components will snag on objects during work tasks. In embodiments, various sensors may protrude inward towards the user such that the user feels the sensor. For example, a pulse rate sensor may include an electrode that protrudes from the inner portion of a wristband 100 to be placed in the anterior distal portion of the user's wrist so as to effectively measure the user's pulse rate for a biometric data read.

FIG. 4 is a flow diagram of an example process 400 for detecting various biometric and environmental hazards and notifying one or more communication devices accordingly, with respect to various embodiments. FIG. 4 is in no way limited to the order as illustrated. For example, operation 404 may occur before operation 402 and operation 410 may occur shortly after operations 404 or 402. Process 400 may start when the wearable sensing device performs operation 402 to receive a plurality of biometric data values through various sensors. The biometric data values may correspond to a health state of a person wearing the sensing device. The sensing device may then perform operation 404 to receive a plurality of environmental data values through various sensors. The environmental data values may correspond to a safety state of an environment the person is in. The sensing device may then perform operation 406 to compare the plurality of biometric data values and the plurality of environmental data values against a respective model of biometric and environmental data values. The models of biometric and environmental data values may specify threshold data values to indicate a likelihood that a person is in an unhealthy state and indicate a likelihood that an environment is in an unsafe state. In various embodiments, the sensing device may perform operation 408 to determine which biometric or environmental data values exceeds any of the model threshold values. If no model threshold values are exceeded (i.e., the person is in a healthy state and the environment is in a safe state), then the process 400 may be repeated to receive continuous feedback regarding a person's health or environment. If one or more biometric or environmental data values exceeds one or more model threshold values, then the sensing device or central server computing device may perform operation 410 to notify one or more communication devices (e.g., provide feedback to the sensing device using e LEDs, notify co-worker' smartphones, etc.) that the person is in an unhealthy state or unsafe environment. According to various embodiments, the person wearing the sensing device may then perform operation 412 to adjust a health or environment state (e.g., take a break to lower heart rate). In various embodiments, the sensing device may continually perform operations 402, 404, 406, and 408 to notify one or more communication devices until the biometric or environmental data values no longer exceeds threshold values (e.g., an alarm will continuously be emitted until the person is in healthy state or safe environment). This may be possible via an alert module in the memory, wherein the alert module continuously polls (e.g., every 5 seconds) the sensing device to make regular reads of biometric and environmental data gathered from a user and the user's environment.

In various embodiments, the sensing device may perform operation 402 to receive biometric data values via multiple sensors. In one or more embodiments, the sensing device may receive biometric data values from an accelerometer sensor. An accelerometer may measure dynamic acceleration forces (e.g., vibration and movement) and static acceleration forces (e.g., gravitational forces) of the sensing device. By utilizing static measurements, an accelerometer sensor may determine a tilt position of the sensing device, which may indicate if a person wearing the device is standing up or laying down for a prolonged period of time. Accordingly, these readings may indicate if a person has passed out or been seriously injured. The accelerometer may also measure sudden changes in dynamic acceleration of the sensing device. For example, a plant operator wearing the sensing device may fall several feet from a unit of equipment and suffer serious injury. Before the plant operator falls, an accelerometer reading may be 1 gravitation force unit (g), indicating that an accelerometer is experiencing regular gravitational forces. However, as the plant operator falls, the accelerometer reading may be 0 g followed by a spike of 5 g, indicating that a person has fallen by accelerating at the rate of gravity and experienced a sharp ground force reaction. In another example, a large vehicle operator may be travelling in a vehicle at a particular acceleration and the accelerometer may detect that an acceleration rate has suddenly spiked or dramatically decreased, indicating a potential crash.

Accelerometers may include single axis, dual axis, or three axis configurations. Accelerometers may also be any suitable type. For example, the accelerometers may be piezoelectric accelerometers, Micro-electromechanical System (MEMS) accelerometers, capacitance accelerometers, or any other type of accelerometer suitable for embodiments of the present disclosure.

In one or more embodiments, the sensing device may receive biometric data values from a gyroscope sensor. A gyroscope may measure the angular velocity of an object in X, Y, and/or Z axes. The gyroscope may accordingly be utilized to measure the angular velocity of the sensing device, and consequently the angular velocity of the user wearing the sensing device. The sensing device may particularly indicate changes in a person's gait pattern or detect sudden rotational movements. For example, a gyroscope may give an initial reading of 0 degrees of rotation per second in a Y and Z plane (i.e., sagittal plane) as a person is walking and the sensing device that the person is wearing is experiencing no sagittal plane rotational movement. However, if the person falls in the sagittal plane, the gyroscope may read that the sensing device is rotating in the sagittal plane at 360 degrees per second. In various embodiments, the gyroscope sensor may be utilized with an accelerometer or compass to obtain exact orientation positioning and more degrees of freedom (i.e., more dimensional measurements). The type of gyroscope may be any suitable gyroscope, such as mechanical gyroscopes, piezoelectric gyroscopes, microelectromechanical gyroscopes (MEMS), or any other gyroscopes appropriate for embodiments of the present disclosure.

In one or more embodiments, the sensing device may receive biometric data values from a pulse oximeter sensor. A pulse oximeter may measure how much oxygen a person's blood is carrying, compared with how much oxygen the person's blood is capable of carrying (i.e., oxygen saturation level). A pulse oximeter may also measure a respiration rate, which measures a quantity of inhalation and exhalation cycles a user is performing over a period of time. A pulse oximeter may also measure a heart rate, which measures a quantity of heart beats over a period of time. In various embodiments, the sensing device may be embedded in a glove. In some embodiments, a pulse oximeter electrode input sensor may be placed at the anterior and distal portion of the first finger portion of the glove. Accordingly, when a person places his or her hand in the glove the corresponding sensor may be disposed on the anterior and distal portion of the first finger to get a proper oxygen saturation level reading from the pulse oximeter. In various embodiments, heart rate, blood saturation levels, and respiration may be measured by different sensors other than a pulse oximeter. For example, a heart-rate monitor device sensor may measure the heart rate, or a breath tracking device may measure the respiration rate.

In various embodiments, the sensing device may be embedded in an armband, which is meant to be worn on a distal portion of the arm (i.e., wrist). A pulse oximeter electrode input sensor may be placed on the anterior portion of the armband, which may protrude towards the inside of the armband. Accordingly, when a person places the armband on his or her wrist, the electrode may be disposed on the anterior and distal portion of his or her wrist just above the palm in order to get an appropriate pulse rate (i.e., heart rate) reading.

In various embodiments, the sensing device may be embedded in a form-fitting shirt. A respiratory rate electrode input sensor may be placed around the upper-mid section of the shirt. Accordingly, when a person places the shirt on, the electrode may be disposed around his or her chest in order to get an appropriate respiration rate reading. In these embodiments, a respiratory rate sensor may determine a quantity of chest expansions in a given amount of time, which would give an indication of a respiration rate.

In one or more embodiments, the sensing device may receive biometric data values from a Galvanic Skin Response (GSR) sensor. The galvanic skin response (also known as electrodermal response) is the change in electrical properties of certain portions of a person's skin, which is caused by an interaction between environmental events and a person's psychological state. This may also referred to as a person's stressed state. When a person is in a particular heightened psychological or physiological aroused state, eccrine glands may produce sweat, which may be conductive and consequently a heighted reading may occur. To measure this response, skin conductance or resistance may be measured. In one example, a worker may have experienced a sudden loss of oxygen in a confined space. Accordingly, the worker may panic and experience an elevated secretion of sweat from the eccrine glands, which may cause an elevated spike in GSR. A GSR sensor may accordingly make the proper elevated reading, and the sensing device may send notifications to several communication devices.

Operation 404 occurs when the sensing device receives a plurality of environmental data values, which may correspond to a safety state of an environment that the user wearing the sensing device is in. In one or more embodiments, the sensing device may receive environmental data values from a temperature sensor. The temperature sensor may be utilized to measure the ambient temperature of an environment so as to ensure that a worker may take precautions while working in an extremely hot environment. For example, a groundskeeper may work in an outside temperature of 110 degrees Fahrenheit. Accordingly, a temperature sensor may read the temperature and notify the groundskeeper to take an appropriate amount of breaks. The type of temperature sensor may be a thermocouple, thermistor, resistance temperature sensor, thermometer, infrared sensor, bimetallic sensors, silicon diode sensors, or any other suitable temperature sensor appropriate to utilize on the sensing device and sense particular environmental states.

In one or more embodiments, the sensing device may receive environmental data values from a microphone. A microphone may be utilized to determine the ambient noise level of an environment that a worker is in. For example, a worker in a data center may be working in a data center with a noise level at 100 dB. The microphone may read the noise level and provide the appropriate data value feedback to the worker that the noise level is 100 dB. In various embodiments, the microphone may be an electrostatic (e.g., electret microphone), dynamic, piezoelectric, sound intensity microphones, or any other suitable type of microphone for detecting sound according to embodiments of the present disclosure.

In one or more embodiments, the sensing device may receive environmental data values from an electromagnetic sensor. In various embodiments the electromagnetic sensors may be various light sensors, such as an ambient light sensors, ultraviolet light sensors, gamma ray sensors, or other electromagnetic sensors that may detect electromagnetic frequencies or wavelengths to determine radiant energy levels. In one example, a welder may be engaged in plasma arc welding. The light produced by the welding may be ultraviolet, emitting at a wavelength of 400 nanometers (nm). The light produced may correspond to a protective shading degree requirement on the face shield in order to minimize eye strain or damage. Accordingly, the light sensor may measure the light energy and provide feedback to the worker (e.g., via an LED) that the worker may need to consider changing face shield shades according to various personal protective equipment (PPE) requirements. In another example, a worker may work in a confined space (e.g., a mine shaft). Accordingly, the sensing device may include an ambient light temperature sensor that determines when there is little or no visible light present in the environment. When the worker enters the confined space with little or no light, an ambient light sensor may determine that no light is available and accordingly, the sensor device may provide visible light such that a worker may see his or her immediate environment.

In one or more embodiments, the sensing device may receive environmental data values from a barometric sensor. A barometric sensor may be a barometer that measures air pressure of a particular environment so as to predict weather changes. For example, a worker may be working in an outside environment at sea level where the barometric sensor is measuring atmospheric pressure at 29.92 inches (i.e., 1013 millibars/1013 hPa). The atmospheric pressure reading may suddenly drop (e.g., after two hours) to 29.4 inches. Accordingly, this may indicate that a storm will soon be present. This may be important for notifying workers whose work tasks are dependent on clear conditions (e.g., working on power lines, electrician tasks, etc.). Barometric sensors may be micro-electromechanical (MEMS), water-based, mercury barometers, aneroid barometers, or any other suitable barometer for embodiments of the present disclosure.

In one or more embodiments, the sensing device may receive environmental data values from a toxic gas sensor. In various embodiments, the toxic gas sensor may detect carbon monoxide, hydrogen sulfide, arsine, bromine, cyanogen, tungsten hexafluoride, or any other toxic gas. In various environments, workers may be exposed to any number of elevated levels of toxic gases. For example, a worker may place a sensing device that is embedded on an armband just within a utility hole (i.e., manhole) to measure the presence of hydrogen sulfide, as opposed to dropping a draw pump through the utility hole to make a measurement, which may be burdensome and time consuming. The types of sensors utilized may be any suitable sensor for embodiments of the present disclosure such as catalytic sensors, electrochemical sensors, thermal conductivity sensors, Non-dispersive Infrared Absorption (NDIR) sensors, metal oxide sensors, photoionization sensors, or any other suitable sensor.

In one or more embodiments, the sensing device may receive environmental data values from oxygen or carbon dioxide level sensors to determine the amount of oxygen or carbon dioxide available in an environment. This may be utilized, for example, when a person is performing a work task in a confined space (e.g., a cavern) that lacks appropriate oxygen for breathing. In various embodiments, the oxygen level or carbon dioxide level sensor may be a semiconducting metal oxide sensor, potentiometric sensor, amperometric sensor, an optical oxygen sensor, or any other suitable sensors for embodiments of the present disclosure.

In one or more embodiments, the sensing device may receive environmental data values from a flammability sensor. A flammability sensor may determine the flammability of an environment. A fire may require an oxidizing agent, such as oxygen, and a fuel source. Accordingly, in one example, a worker may utilize an oxygen level sensor described above to determine if a threshold amount of oxygen is available (e.g., 16% oxygen) in order for a fire to be present. A worker may then utilize a flammability sensor (e.g., a catalytic flammability detector) to determine the flammability of a gas that is present in the air or other material. The flammability sensor may accordingly detect flammable gases such as acetylene, ammonia, hydrogen, propane, propylene, methane or any other flammable gas. This may be useful for a person engaged in spark or fire-related work tasks, such as welding, to avoid combustible environments. The flammability sensor type may be catalytic (i.e., pellistor), Field Effect Transistor (FET), electrical conductivity change sensors, or any other suitable sensor.

Figure 5A:
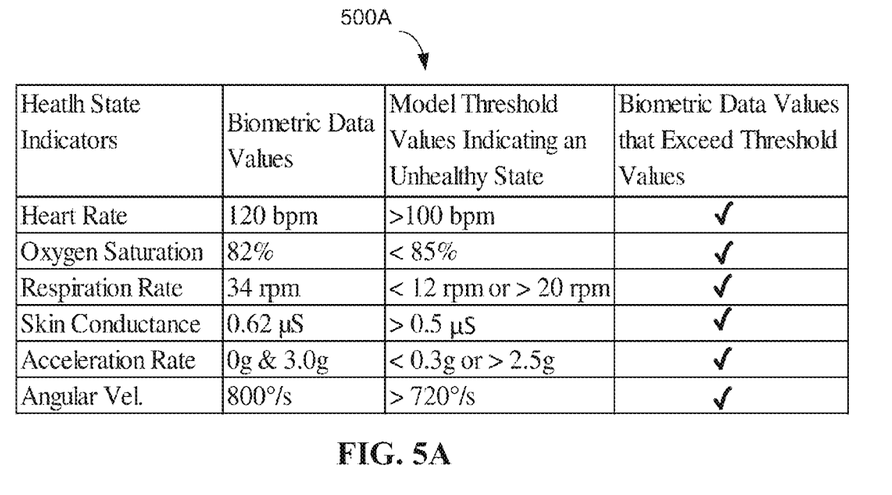
FIG. 5A illustrates a table of biometric data values, corresponding model threshold data values, and indications of which biometric data values exceed the model threshold values, according to various embodiments.
Figure 5B:
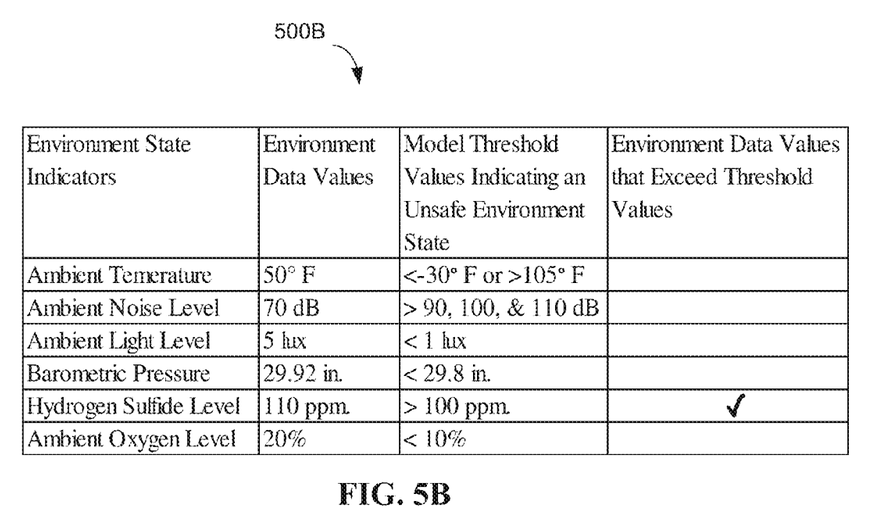
FIG. 5B illustrates a table of environmental data values, corresponding model threshold data values, and indications of which environmental data values exceed the model threshold values, according to various embodiments.

In operation 406, the sensing device (or remote server) may compare the plurality of biometric data values and the plurality of environmental data values against models of biometric data values and models of environmental data values. The models of biometric and environmental data values may specify threshold data values to indicate a likelihood of a person in an unhealthy state and a likelihood that an environment is in an unsafe state. For example, FIGS. 5A and 5B illustrate tables of biometric data values, environmental data values, corresponding model threshold data values, and indications of which biometric and environmental data values exceeds the model threshold values, according to various embodiments. In an example, the biometric and environment data values in FIGS. 5A and 5B may be illustrative of a worker who has experienced hydrogen sulfide toxic gas poisoning in a confined space (e.g., mine shaft), has experienced resulting stress, and has experienced various erratic movements (convulsions) and has fallen.

FIG. 5A shows table 500A according to one or more embodiments, which includes various health state indicators, a plurality of biometric data values, a plurality of model threshold values, and indications for which biometric data values exceed model threshold values. A heart rate sensor on a sensing device may measure a person's heart rate to be 120 beats per minute (bpm). The model threshold value indicates than an unhealthy heart rate is any value greater than 100 bpm. Accordingly, the person's heart rate value has exceeded the threshold value as indicated by the checkmark. A pulse oximeter on the sensing device may measure the person's oxygen saturation to be 82% (i.e., the person's blood is carrying 82% of the oxygen that the blood is capable of carrying). The threshold value may indicate that any value less than 85% is unhealthy. Accordingly, the oxygen saturation value has exceeded the threshold value indicating an unhealthy state. A pulse oximeter on the sensing device may measure the person's respiration rate at 34 respirations per minute (rpm). The model threshold values indicate that an unhealthy respiration rate may be less than 12 rpm but greater than 20 rpm. Accordingly, the person's respiration rate exceeds the 20 rpm threshold value indicating an unhealthy state.

A GSR sensor on the sensing device may measure the person's skin conductance at 0.62 microsiemens (µS). The threshold value may be any measurement greater than 0.5 µS. Accordingly, the person's skin conductance reading exceeds the threshold. An accelerometer sensor on the sensing device may measure that the person's acceleration rate was 0 g at a particular point in time (indicating a free fall), and sharply spiked to 3.0 g (indicating a hard impact with the ground). The threshold values may be less than 0.3 g or greater than 2.5 g. The person's acceleration has exceeded both of these threshold values, indicating a fall. A gyroscope sensor on the sensing device may read that the person's angular velocity in one or more planes is 800 degrees per second (°/S). The threshold value for this plane may be any value greater than 720°/s. Therefore, the person may have experienced sudden rotational movements from a fall. The accelerometer and gyroscope may also provide adequate feedback to indicate that the person is experiencing convulsions. For example, an accelerometer and gyroscope may detect that a person is experiencing short durational accelerations in the limbs (e.g., the sensing device is on the wrist), that the person is in a tilted position such that he or she is laying on the ground, and that the person is rapidly rotating his or her limbs. If these unusual movements occur for a specified amount of time, an inference of convulsions may be determined. As described below, the source of the tremors may be further inferred from the presence of sulfide gas in the environment.

FIG. 5B shows table 500B according to one or more embodiments, which includes various environment state indicators, a plurality of environment data values, a plurality of model threshold values, and indications for which environment data values exceeds model threshold values. A temperature sensor on the sensing device may measure the ambient temperature to be 50 degrees Fahrenheit (F.). The model threshold values for which temperatures may be at dangerous levels may be any temperature below −30 degrees F. or above 105 degrees F. A microphone on the sensing device may measure the noise level at 70 decibels (dB). In this example, there may be three model threshold values such that the sensing device transmits a notification signal when each of the 90, 100, and 110 dB thresholds have been met. These model values may correspond to PPE OSHA model thresholds. For example, at 90 dB, a person is required to put on hearing protection after 8 hours. At 100 dB, a person is required to put on hearing protection after 2 hours. At 110 dB, a person is required to put on hearing protection only after a half hour. An ambient light level sensor on the sensing device may measure the ambient light level at 5 luminance (lux). The model threshold value may be any value less than 1 lux (indicating night or dark levels). A barometric sensor on a sensing device may measure the barometric pressure to be 29.92 inches (in.). The model threshold value indicating a potential change in weather may be less than 29.8 in. A toxic gas sensor on the sensing device may measure a hydrogen sulfide level to be 110 parts per million (ppm). The model threshold value at which point unsafe levels of hydrogen sulfide are present may be any value greater than 100 ppm. Accordingly, the hydrogen sulfide measurement of the environment exceeds the respective model threshold value. An oxygen level sensor on the sensing device may measure that a person is breathing in 20% oxygen. The threshold value for which the oxygen level is too low to sustain consciousness may be any value less than 10%. Accordingly, FIGS. 5A and 5B may be indicative of a person who has experienced hydrogen sulfide gas poisoning and has consequently experienced shortness of breath, tremors, a fall, and other serious physiological side effects.

Referring back to FIG. 4, according to various embodiments, in operation 408, if one or more biometric or environmental values exceeds at least one of the model threshold values, the sensing device or server may notify various communication devices according to operation 410. In alternative embodiments, however, if none of the biometric or data values surpass model threshold values, the sensing device may still notify communication devices specifying that neither the biometric data values nor the environmental data values exceed any of the threshold data values. These notifications may be made to ensure that a worker's sensing device (including all of the sensors) is properly working.

In various embodiments, the sensing device may notify by providing immediate feedback to an output device located on the sensing device. For example, the feedback and output device may be flashing LEDs as illustrated in FIG. 2, auditory feedback such as emitting a tone, tactile feedback (e.g., vibration through the vibration board), or any other suitable feedback. In various embodiments, the sensing device may also notify secondary devices located on the person. For example, with the radio capabilities of the sensing device, the sensing device may transmit a signal to a mobile phone, smart watch, smart glasses, or any other secondary device located on the person wearing the sensing device for the notification. In various embodiments, the notifications may be text messages to the mobile phone, auditory notifications, vibration notifications, or any other type of suitable notification to the secondary devices. In various embodiments, after the notification has been transmitted to a mobile phone, the mobile phone may provide indicia indicating which biometric or environmental data values exceed model thresholds. For example, tables analogous to 500A and 500B may be transmitted to the worker's mobile phone.

In various embodiments, the notification according to operation 410 may be transmitted to external secondary communication devices. For example, the sensing device may notify a supervisor's mobile phone, smart watch, smart glasses, or any other secondary device located on the supervisor or any other co-worker. In another example, the sensing device may notify a remote server and the server may notify one or more parties (e.g., worker wearing sensing device, supervisor, co-worker, etc.).

In various embodiments, the sensing device or server may notify various communication devices even if one biometric or environmental data value is above a model threshold value. In other embodiments, the notification may be based on a combination of model thresholds being exceeded. For example, a skin conductance reading may be the only data value above a model threshold value, which may indicate that a person is stressed with factors outside of a work environment. Accordingly, a notification may not be performed. However, if skin conductance, heart rate, acceleration, and oxygen level model thresholds have all been met around the same time period, it may indicate sudden trauma experienced by a worker during a work task. Accordingly, an alert module in the sensing device may require a combination of thresholds being met according to various health or environment indicators to issue a notification.

In various embodiments, after the notification has been performed in operation 410, the person wearing the sensing device may adjust his health state or environment state. For example, if carbon monoxide levels are above a model threshold in a room, the person may walk out of the room. If the person's heart rate is elevated past a threshold, the person may take a break. In various embodiments, whether the person adjusts his or her state or not after the notification has occurred, operations 402, 404, 406, and 408 may continuously occur until the biometric or environmental data values are stabilized (i.e., a notification will continuously be signaled until the biometric or environmental values are not exceeding model threshold values). In other embodiments, the notification may only occur for a predetermined amount of time (e.g., 2 minutes) regardless of whether or not the data values have been stabilized. In other embodiments, the person wearing the sensing device may have the option to turn off the notification with a switch on the sensing device.

Figure 6:
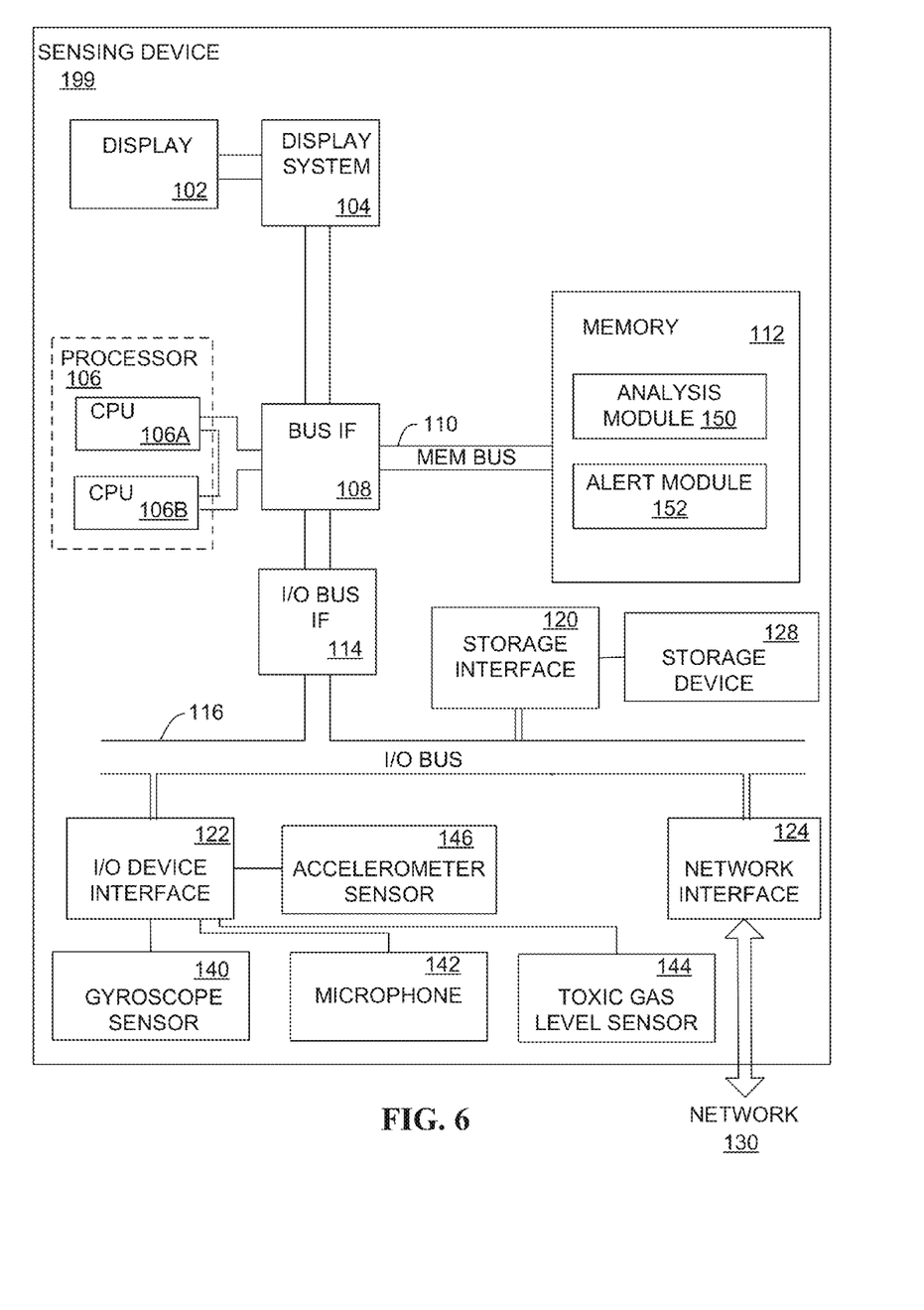
FIG. 6 is a block diagram illustrating another example of a sensing device, according to embodiments.

FIG. 6 is a block diagram illustrating another example of a sensing device, according to embodiments. The components of the sensing device 199 can include one or more processors 106, a memory 112, a storage interface 120, an Input/Output ("I/O") device interface 122, and a network interface 124, all of which are communicatively coupled, directly or indirectly, for inter-component communication via a memory bus 110, an I/O bus 116, bus interface unit ("IF") 108, and an I/O bus interface unit 114. The I/O device interface may be connected to various sensors, such as a gyroscope sensor 140, a microphone 142, a toxic gas level sensor 144, and an accelerometer sensor 146.

The sensing device 199 may include one or more general-purpose programmable central processing units (CPUs) 106A and 106B, herein generically referred to as the processor 106. In an embodiment, the sensing device 199 may contain multiple processors; however, in another embodiment, the sensing device 199 may alternatively be a single CPU device. Each processor 106 executes instructions stored in the memory 112.

The sensing device 199 may include a bus interface unit 108 to handle communications among the processor 106, the memory 112, the display system 104, and the I/O bus interface unit 114. The I/O bus interface unit 114 may be coupled with the I/O bus 116 for transferring data to and from the various I/O units. The I/O bus interface unit 114 may communicate with multiple I/O interface units 120, 122, and 124, which are also known as I/O processors (IOPs) or I/O adapters (IOAs), through the I/O bus 116. The display system 104 may include a display controller, a display memory, or both. The display controller may provide video, audio, or both types of data to a display device 102. The display memory may be a dedicated memory for buffering video data. The display system 104 may be coupled with a display device 102, such as a standalone display screen, computer monitor, television, a tablet or handheld device display, or another other displayable device. In an embodiment, the display device 102 may include one or more speakers for rendering audio. Alternatively, one or more speakers for rendering audio may be coupled with an I/O interface unit. In alternate embodiments, one or more functions provided by the display system 104 may be on board an integrated circuit that also includes the processor 106. In addition, one or more of the functions provided by the bus interface unit 108 may be on board an integrated circuit that also includes the processor 106.

The I/O interface units support communication with a variety of storage and I/O devices. For example, the I/O device interface 122 supports the attachment of one or more user I/O devices, which may include a gyroscope sensor 140, a microphone 142, a toxic gas level sensor 144, and an accelerometer sensor 146 all configured together to receive a plurality of biometric and environmental data values so as to enable an assessment of a person's health state and environmental state that the person is in, as described above.

The storage interface 120 supports the attachment of one or more disk drives or direct access storage devices 128 (which are typically rotating magnetic disk drive storage devices, although they could alternatively be other storage devices, including arrays of disk drives configured to appear as a single large storage device to a host computer, or solid-state drives, such as a flash memory). In another embodiment, the storage device 128 may be implemented via any type of secondary storage device. The contents of the memory 112, or any portion thereof, may be stored to and retrieved from the storage device 128 as needed. The I/O device interface 122 provides an interface to any of various other I/O devices or devices of other types, such as printers or fax machines. The network interface 124 provides one or more communication paths from the sensing device 199 to other digital devices and computer systems.

Although the sensing device 199 shown in FIG. 6 illustrates a particular bus structure providing a direct communication path among the processors 106, the memory 112, the bus interface 108, the display system 104, and the I/O bus interface unit 114, in alternative embodiments the sensing device 199 may include different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface unit 114 and the I/O bus 108 are shown as single respective units, the sensing device 199 may include multiple I/O bus interface units 114 and/or multiple I/O buses 116. While multiple I/O interface units are shown, which separate the I/O bus 116 from various communication paths running to the various I/O devices, in other embodiments, some or all of the I/O devices are connected directly to one or more system I/O buses.

In an embodiment, the memory 112 may include a random-access semiconductor memory, storage device, or storage medium (either volatile or non-volatile) for storing or encoding data and programs. In another embodiment, the memory 112 represents the entire virtual memory of the sensing device 199, and may also include the virtual memory of other computer systems coupled to the sensing device 199 or connected via a network 130. The memory 112 may be a single monolithic entity, but in other embodiments the memory 112 may include a hierarchy of caches and other memory devices. For example, memory may exist in multiple levels of caches, and these caches may be further divided by function, so that one cache holds instructions while another holds non-instruction data, which is used by the processor. Memory 112 may be further distributed and associated with different CPUs or sets of CPUs, as is known in any various so-called non-uniform memory access (NUMA) computer architectures.

The memory 112 may store all or a portion of the components and data utilized for embodiments of the present disclosure. For example the memory 112 may include components to be executed by the processor 106, such as an analysis module 150 configured to compare various biometric and environmental data values against respective model data values, as described above. Further, the memory 112 may include an alert module 152 configured to notify one or more communication devices, as described above. These programs and data structures are illustrated in FIG. 6 as being included within the memory 112 in the sensing device 199; however, in other embodiments, some or all of them may be on different computer systems and may be accessed remotely, e.g., via a network 130. The sensing device 199 may use virtual addressing mechanisms that allow the programs of the sensing device 199 to behave as if they only have access to a large, single storage entity instead of access to multiple, smaller storage entities. Thus, while the components and data shown in FIG. 6 are illustrated as being included within the memory 112, these components and data are not necessarily all completely contained in the same storage device at the same time. Although the components and data shown in FIG. 6 are illustrated as being separate entities, in other embodiments some of them, portions of some of them, or all of them may be packaged together.

In an embodiment, the components shown in FIG. 6 may be implemented in hardware via semiconductor devices, chips, logical gates, circuits, circuit cards, and/or other physical hardware devices in lieu of, or in addition to, a processor-based system. In an embodiment, the components shown in FIG. 6 may include data in addition to instructions or statements.

FIG. 6 is intended to depict representative components of the sensing device 199. Individual components, however, may have greater complexity than represented in FIG. 6. In FIG. 6, components other than or in addition to those shown may be present, and the number, type, and configuration of such components may vary. Several particular examples of additional complexity or additional variations are disclosed herein; these are by way of example only and are not necessarily the only such variations. The various program components illustrated in FIG. 6 may be implemented, in various embodiments, in a number of different ways, including using various computer applications, routines, components, programs, objects, modules, data structures, etc.

Aspects of the present invention may be a system, a method, and/or a computer program product. The computer program product may include a computer readable storage medium (or media) having computer readable program instructions thereon for causing a processor to carry out aspects of the various embodiments.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of embodiments of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of embodiments of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A method for detecting and notifying of various potential hazards, comprising:

receiving a plurality of biometric data values by a first set of sensors of a sensing device, the biometric data values corresponding to a health state of a person;

receiving a plurality of environmental data values by a second set of sensors of the sensing device, the environmental data values corresponding to a safety state of an environment that the person is in, wherein at least one of the plurality of biometric sensors or at least one of the plurality of environmental sensors include one or more apertures lined with conductive material, and wherein a conductive threading configured to pass through the one or more apertures on the conductive material to sew the at least one of the plurality of biometric sensors or the at least one of the plurality of environmental sensors to a wearable article, and wherein the conductive threading further provides a transfer medium for transferring data from the at least one of the plurality of biometric sensors or the at least one of the plurality of environmental sensors to a processor;

comparing, by the sensing device, the plurality of biometric data values against a respective model of biometric data values and comparing, by the sensing device, the plurality of environmental data values against a respective model of environmental data values, the respective model of biometric data values specifying threshold data values that indicate a likelihood of a person in an unhealthy state and the respective model of environmental data values specifying threshold data values that indicate a likelihood that an environment is in an unsafe state;

in response to the comparing, determining that at least one of the biometric data values or the environmental data values exceeds at least one of the threshold data values; and notifying one or more communication devices based on the determining that the at least one of the biometric data values or the environmental data values exceeds the at least one of the threshold data values.

2. The method of claim 1, wherein the notifying one or more communication devices includes notifying, by the sensing device, the sensing device, the notifying includes causing a first set of LEDs of a plurality of LEDs within the sensing device to flash in response to the determining at least one of the biometric data values exceeds at least one of the threshold data values that indicates a likelihood of a person in an unhealthy state, the sensing device further including a second set of LEDs of the plurality of LEDS that are configured to flash in response to determining a likelihood that the person is in a second unhealthy state.

3. The method of claim 1, wherein the receiving of the plurality of biometric data values includes receiving data values indicating a galvanic skin response (GSR) of the person wearing the sensing device as an article of clothing.

4. The method of claim 1, wherein the receiving of the plurality of environmental data values includes receiving data values indicating air pressure of the environment.

5. The method of claim 1, further comprising:
   in response to the comparing, determining, by the sensing device, that at least one of the environmental data values exceeds the threshold data values that indicates a likelihood that an environment is in an unsafe state; and
   notifying, by the sensing device, one or more communication devices that the environmental data values exceeds at least one of the threshold data values that indicates a likelihood that an environment is in an unsafe state.

6. A sensing device for detecting and notifying of various hazards, comprising:
   a plurality of biometric sensors configured to receive a plurality of biometric data values corresponding to a health state of a person, wherein the plurality of biometric sensors includes at least a gyroscope sensor configured to measure an angular velocity of the person;
   a plurality of environmental sensors configured to receive a plurality of environmental data values corresponding to a safety state of an environment that the person is in;
   conductive threading configured to stitch-fasten at least the plurality of biometric sensors and the plurality of environmental sensors to an article of clothing, and further configured to provide communication channels for the plurality of biometric sensors and the plurality of environmental sensors;
   an analysis module configured to compare the plurality of biometric data values against a respective model of biometric data values, and further configured to compare the plurality of environmental data values against a respective model of environmental data values, the respective model of biometric data values specifying threshold data values that indicate a likelihood of a person in an unhealthy state and the respective model of environmental data values specifying threshold data values that indicate a likelihood that an environment is in an unsafe state; and
   an alert module configured to notify one or more communication devices when the environmental data values or biometric data values exceeds the threshold data values that indicates a likelihood of a person in an unhealthy state or the threshold data values that indicates a likelihood that an environment is in an unsafe state.

7. The sensing device of claim 6, wherein the article of clothing is a sweat armband, wherein a first portion of the sensing device is covered and encased by the armband and a second portion of the sensing device protrudes out from the armband, the first portion that is covered includes the conductive threading and the processor, the second portion that is not covered includes at least one sensor.

8. The sensing device of claim 6, wherein the plurality of biometric sensors includes an accelerometer sensor configured to determine an acceleration rate of the person.

9. The sensing device of claim 6, wherein the plurality of environmental sensors includes a microphone configured to determine a noise level of the environment.

10. The sensing device of claim 6, wherein the plurality of environmental sensors includes a temperature sensor configured to determine an ambient temperature of the environment.

11. The sensing device of claim 6, wherein the plurality of biometric sensors includes a pulse oximeter sensor configured to determine an oxygen saturation level, a respiration rate, and a heart rate of the person.

12. The sensing device of claim 6, wherein the plurality of environmental sensors includes an electromagnetic sensor configured to determine an ambient light intensity, an ultra-violet light intensity, and a gamma ray intensity of the environment.

13. The sensing device of claim 6, wherein the plurality of environmental sensors includes a sensor configured to measure a toxic gas level of the environment.

14. The sensing device of claim 6, wherein the alert module includes a radio configured to perform the notifying of one or more communication devices by transmitting a signal to the one or more communication devices specifying that the environment is likely in an unsafe state or the person is likely in an unhealthy state.

15. A computer program product comprising a computer readable storage medium having program code embodied therewith, the program code comprising computer readable program code configured for:
   receiving a plurality of biometric data values by a first set of sensors of a sensing device, the first set of sensors being included with a plurality of sensors, the sensing device including a processor on a microcontroller board and the plurality of sensors, the microcontroller board and the plurality of sensors being sewn, with conductive threading, to a wearable item, wherein the biometric data values corresponding to a health state of a person, wherein the first set of sensors includes at least a gyroscope sensor to measure an angular velocity of the person;
   receiving a plurality of environmental data values by a second set of sensors of the plurality of sensors, the environmental data values corresponding to a safety state of an environment that the person is in, wherein the second set of sensors includes at least a sensor to measure a toxic gas level of the environment;
   comparing, by the sensing device, the plurality of biometric data values against a respective model of biometric data values and comparing, by the sensing device, the plurality of environmental data values against a respective model of environmental data values, the respective model of biometric data values specifying threshold data values that indicate a likelihood of a person in an unhealthy state and the respective model of environmental data values specifying threshold data values that indicate a likelihood that an environment is in an unsafe state;
   in response to the comparing, whether any of the biometric data values or the environmental data values exceed the threshold data values; and
   notifying one or more communication devices based on the whether any of the biometric data values or the environmental data values exceed the threshold data values.

16. The computer program product of claim 15, wherein the receiving of the plurality of environmental data values includes receiving data values indicating a flammability level of the environment the first user is in.

17. The computer program product of claim 15, wherein the notifying of one or more communication devices includes transmitting a signal to a mobile phone, the signal specifying that the biometric data values indicate a likelihood that the person is in a healthy state and the signal specifying that the environmental data values indicate a likelihood that the environment is in a safe state.

18. The computer program product of claim 15, wherein the one or more communication devices includes the sensing device.

19. The computer program product of claim 15, wherein the notifying of one or more communication devices includes providing a visual feedback notification to the sensing device via one or more light emitting diodes (LEDs) located within the sensing device.

\* \* \* \* \*